US005194374A

United States Patent [19]

Rambach

[11] Patent Number: 5,194,374

[45] Date of Patent: Mar. 16, 1993

[54] ISOLATING MEDIUM FOR IDENTIFYING THE SALMONELLA BACTERIUM

[75] Inventor: Alain Rambach, Paris, France

[73] Assignee: EUREC, France

[21] Appl. No.: 819,478

[22] Filed: Jan. 10, 1992

Related U.S. Application Data

[62] Division of Ser. No. 510,903, Apr. 19, 1990, Pat. No. 5,098,832.

[51] Int. Cl.[5] .......................... C12Q 1/04; C12Q 1/02; C12N 1/00; C12N 5/00

[52] U.S. Cl. .......................................... 435/34; 435/29; 435/879; 435/240.54

[58] Field of Search ............... 435/29, 34, 879, 240.54

[56] References Cited

PUBLICATIONS

Baldoma et al *J. Bacteriology* Jun. 1988 vol. 170, No. 6 pp. 2884–2885.

Obradors et al *J. Bacteriology* May 1988 vol. 170, No. 5, pp. 2159–2162.

*Primary Examiner*—Douglas W. Robinson
*Assistant Examiner*—Jane Williams
*Attorney, Agent, or Firm*—Blakely, Sokoloff, Taylor & Zafman

[57] ABSTRACT

The present invention relates to an isolating medium for the identification of the Salmonella bacterium, wherein a polyol metabolizable by Salmonella and a pH indicator reacting to acidification are added to a culture support containing peptones.

9 Claims, No Drawings

ISOLATING MEDIUM FOR IDENTIFYING THE SALMONELLA BACTERIUM

This is a divisional of application Ser. No. 07/510,903, now U.S. Pat. No. 5,098,832, filed on Apr. 19, 1990, by the same inventor.

The present invention relates to an isolating medium enabling the identification of bacteria of the Salmonella species.

The identification of the Salmonella bacterium, which is pathogenic for man, is a major problem in medical bacteriology and in agro-foodstuffs hygiene monitoring.

Thus, in the case of epidemics transmitted by battery hens, the poultry infested in the region of the intestinal tract are not ill but constitute a reservoir of Salmonella. The latter can be spread, in particular by the eggs, in the food chain after these epidemics. Moreover, Salmonella is a bacterium subject to mandatory declaration.

It is now becoming necessary to provide for large scale implementation of the detection of sites, and more particularly farms, infected by the Salmonella bacterium, in order to reduce these epidemics.

In fact, Salmonella are generally to be recognized amongst the commensal species *Escherichia coli* and Proteus.

The detection of Salmonella is customarily carried out on an agar isolating medium which is selective for enterobacteria, enabling pathogenic enterobacteria to be differentiated and suspect Salmonella colonies to be detected. An ideal isolating medium must permit the growth of enterobacteria, the differentiation of the various species present in order to enable subsequent identification of a colony of each type, and the detection of suspect Salmonella colonies.

However, the media of the prior art for isolating enterobacteria only partially ensure the detection of Salmonella. In fact, frequent commensal bacteria of the type *Proteus mirabilis* are found, which give false positive results in these media.

Amongst the proposed agar selective media, the Hektoen medium is generally preferred although being one of the more expensive.

Thus, on this Hektoen medium Salmonella bacteria give blue colonies with a black center ($lac^-sac^-sal^-H_2S^+$) and the mirabilis bacterium, which has the same properties, likewise gives blue colonies with a black center. These false positive results therefore necessitate additional work and expenditure because they make it obligatory to carry out a subsequent examination of several suspect colonies instead of one, possibly without a positive result, not to speak of the risk of diagnostic error after a rapid reading.

Moreover, the ambiguity in the Salmonella response also requires a higher qualification for proceeding to the subsequent step of reisolation of colonies and biochemical differentiation than for a simple recognition of a coloration of colonies. The biochemical differentiation, finally, can slow down the identification and thus impose an additional delay.

The object of the present invention is precisely to remedy these drawbacks and to propose an isolating medium enabling Salmonella colonies to be detected in a non-ambiguous manner by a specific coloration of the colony. In fact, the present invention does not use the conventional Salmonella marking characters $H_2S^+lac^-sac^-sal^-$, which allow Proteus to appear as false positives.

More precisely, the present invention relates to an isolating medium for the identification of the Salmonella bacterium, wherein a polyol metabolizable by Salmonella and a pH indicator reacting to acidification are added to a culture support containing peptones.

According to a particular embodiment of the invention, this polyol metabolizable by Salmonella is adsorbed on a pulverulent material.

The material used has a small particle size, that is to say preferably of less than about 100μ, so as to enable efficient adsorption of the said polyol and to ensure a good fluidity of the powder thus obtained.

Thus, the pulverulent material used is preferably fine silica and more particularly silica gel. However, other types of material, such as cellulose, can also be used.

Amongst the polyols which may be used, those which may be mentioned more particularly are the diols containing 2 to 10 carbon atoms, such as ethanediol, the propanediols and the butanediols, in particular 1,2-propanediol. These diols are, in fact, metabolized by the Salmonella bacterium to give acid species capable of causing pH indicators such as neutral red to react. In contrast, the commensal species such as *E. coli* and Proteus do not give this type of reaction.

This medium can be used more particularly for the detection of foodstuffs Salmonella, all of which give positive results on this medium. For carrying out the process it is preferred to use agar culture media appropriate for the culture of colonies which enables the Salmonella colonies to be identified more rapidly.

Amongst the media which promote the development of enterobacteria, for example, a medium containing deoxycholate could be used. If it is desired to increase the accuracy of the detection, it is possible to add to the medium in question a beta-galactosidase substrate, in particular a chromogenic substrate of the latter of the bromochloroindoxylgalactoside, bromonaphthylgalactoside or hydroxyquinolinegalactoside type, if appropriate in the presence of an inductor, such as IPTG. In fact, as the Salmonella strain is beta $gal^-$, it does not react on this substrate.

The value of the polyols according to the invention, when the above two identification characters are used, is that the presence of polyols does not mask the beta $gal^+$ character, in contrast to the majority of carbohydrates, which, by catabolic repression, are able to mask the beta $gal^+$ character. When these two identification characters are visualized by color reactions, the various types of bacteria, in particular Salmonella, Proteus and *E. coli*, can be identified by a judicious choice. Thus, neutral red as pH indicator and X-gal as beta-galactosidase substrate enable Salmonella to be distinguished from *E. coli*, Citrobacter and Proteus in a mixture containing them, as will be apparent on reading the examples below.

Of course, it is possible in this type of medium to use other negative Salmonella characters, for example beta $glu^-$; in this case a beta-glucosidase substrate will be used.

Likewise, it is possible, rather than using an agar medium, in particular sheets, to use other supports such as a paper or column support and even to detect in the medium itself.

The present invention also relates to a process permitting the identification of Salmonella, in which process the sample is cultured on a medium according to the invention and the presence of Salmonella is detected by the reaction of the pH indicator to the acidification of the medium.

The examples given below as non-limiting examples enable other advantages and characteristics of the present invention to be shown.

EXAMPLE 1

Isolating Medium Permitting the Detection of Salmonella

A medium having the following composition is produced:

| Constituents | g/liter of water |
|---|---|
| 1,2-Propanediol | 5 |
| Peptones | 5 |
| Yeast extract | 2 |
| Deoxycholate | 1 |
| Bromochloroindoxylgalactoside | 0.1 |
| Neutral red | 0.03 |
| Agar | 15 |

By inoculating this medium with various types of enterobacteria and after culturing for 48 hours, the following results are obtained: the Salmonella give red colonies, the *E. coli* blue-green colonies, the Citrobacter blue-violet colonies and the Proteus colorless colonies.

EXAMPLE 2

Isolating medium according to the invention, the polyol being adsorbed on a pulverulent material.

The mixture used has the following composition:

| Constituents | g/liter of water |
|---|---|
| 1,2-Propanediol/silica gel (10 g/16 g) | 26 |
| Peptones | 5 |
| Yeast extract | 2 |
| Deoxycholate | 1 |
| Bromochloroindoxylgalactoside | 0.1 |
| Neutral red | 0.03 |
| Agar | 15 |

By inoculating this medium with various types of enterobacteria and after culturing for 48 hours, results are obtained which are analogous to those observed with the culture medium which was the subject of Example 1, that is to say: the Salmonella give red colonies, the *E. coli* blue-green colonies, the Citrobacter blue-violet colonies and the Proteus colorless colonies.

I claim:

1. An isolating medium for the identification of the Salmonella bacterium, wherein 1,2-propanediol metabolizable by Salmonella and a pH indicator reacting to acidification are added to a culture support containing peptones.

2. The isolating medium as claimed in claim 1, wherein the 1,2-propanediol metabolizable by Salmonella is adsorbed on a pulverulent material.

3. The isolating medium as claimed in claim 2, wherein the pulverulent material has a particle size of less than about 100μ.

4. The isolating medium as claimed in claim 2, wherein the pulverulant material is selected from the group consisting of fine silica, silica gel and cellulose.

5. The isolating medium as claimed in one of claims 1 to 4, wherein the pH indicator is neutral red.

6. The isolating medium as claimed in one of claims 1 to 4, wherein the culture support is an agar medium appropriate for the culture of colonies.

7. The isolating medium as claimed in one of claims 1 to 4, wherein the medium also contains deoxycholates.

8. The isolating medium as claimed in one of claims 1 to 4, wherein the medium also contains a chromogenic beta-galactosidase substrate.

9. The isolating medium as claimed in one of claims 1 to 4, which also contains isopropyl-beta-D-thiogalactopyranoside (IPTG).

* * * * *